United States Patent [19]

Sutherland

[11] 4,258,716
[45] Mar. 31, 1981

[54] MICROSURGICAL INSTRUMENTS

[75] Inventor: Geoffrey Sutherland, Melbourne, Australia

[73] Assignee: The University of Melbourne, Parkville, Australia

[21] Appl. No.: 7,778

[22] Filed: Jan. 30, 1979

[30] Foreign Application Priority Data

Feb. 6, 1978 [AU] Australia .............. PD3258

[51] Int. Cl.³ .............. A61B 17/32; A61B 17/28
[52] U.S. Cl. .............................. 128/318; 128/321
[58] Field of Search .............. 128/321, 305, 317, 346, 128/351-355, 318; 30/240, 209, 29

[56] References Cited

U.S. PATENT DOCUMENTS

| 984,756 | 2/1911 | Frisch | 128/321 |
|---|---|---|---|
| 2,137,710 | 11/1938 | Anderson | 128/321 |
| 2,708,437 | 5/1955 | Hutchins | 128/751 X |
| 2,790,437 | 4/1957 | Moore | 128/751 |
| 2,894,324 | 7/1959 | Hardin | 30/240 |
| 3,995,619 | 12/1976 | Glatzer | 128/754 X |

Primary Examiner—Robert W. Michell
Assistant Examiner—Michael H. Thaler
Attorney, Agent, or Firm—Dennison, Meserole, Pollack & Scheiner

[57] ABSTRACT

Microsurgical instruments having a handle adapted to be grasped by a surgeon and operating means on the handle and an instrument body extending outwardly from the handle and having on its outer end the operative portion of the instrument which may be, for example, scissors or forceps, the arrangement being such that the instrument body can be freely rotated about the axis of the handle to align the instrument in the required position and which body is located frictionally in position when the operating means is actuated.

9 Claims, 15 Drawing Figures

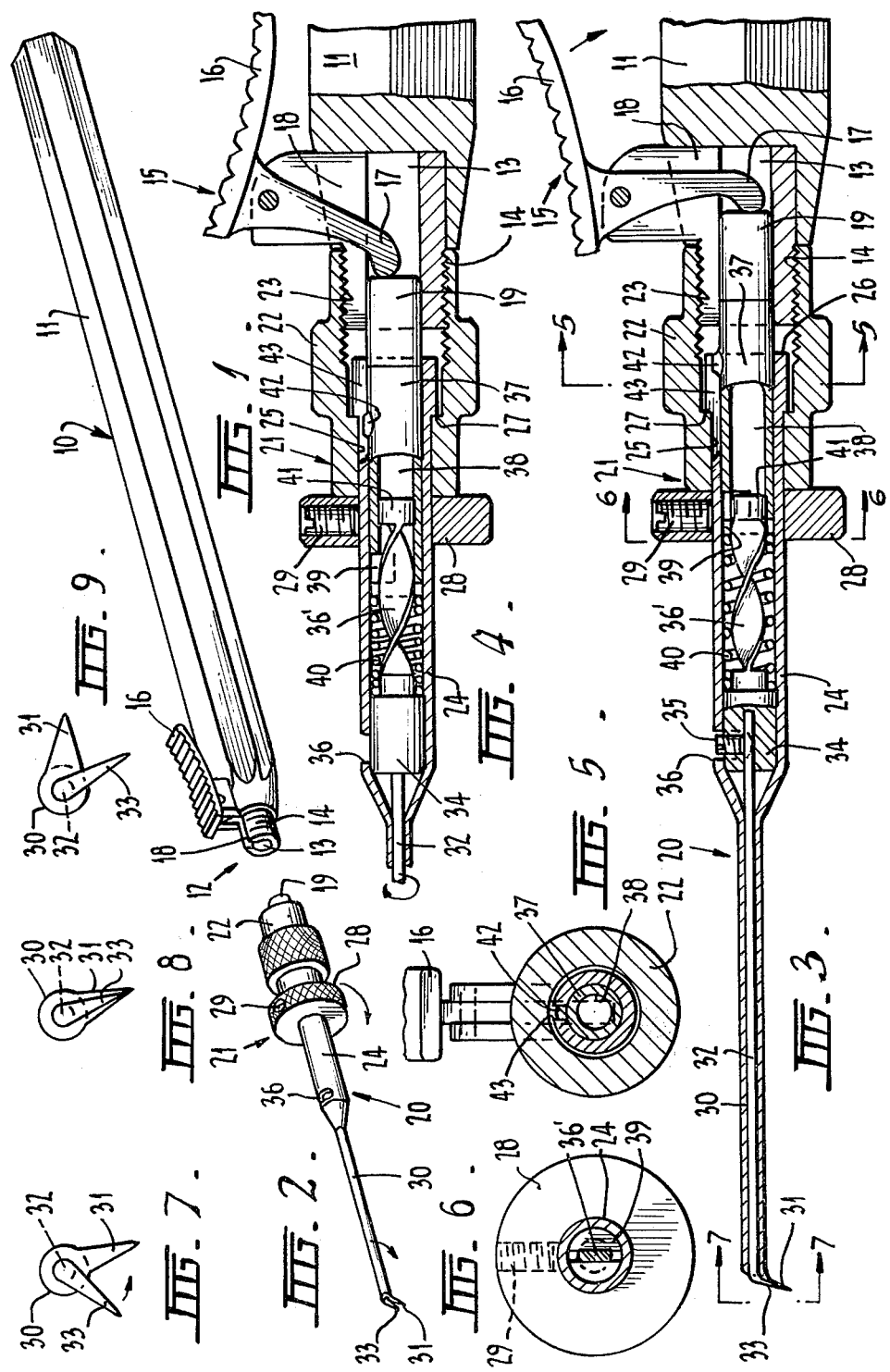

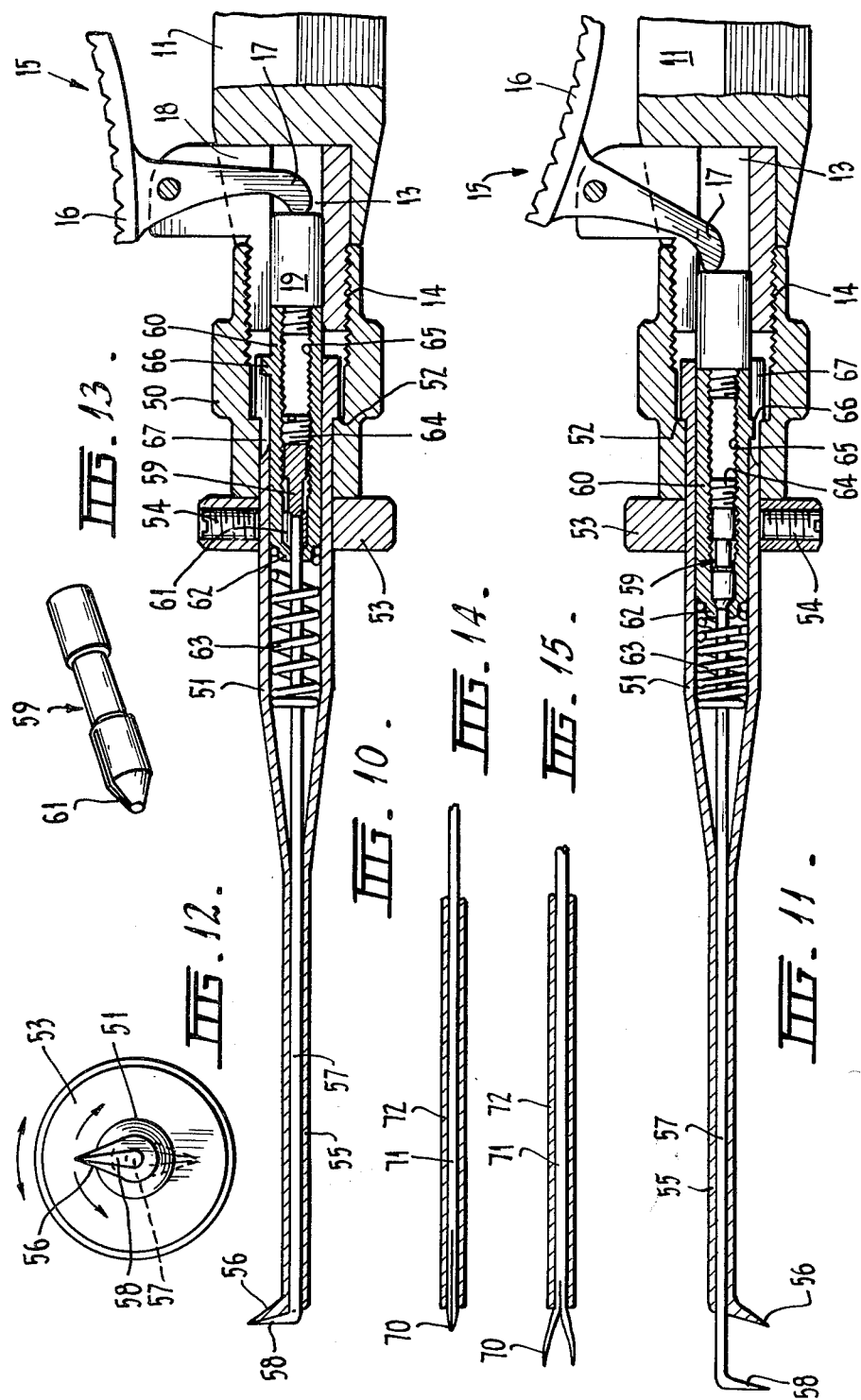

MICROSURGICAL INSTRUMENTS

This invention relates to improved microsurgical instruments and particularly to improved microsurgical instruments which are finger operated by a surgeon.

In microsurgery it is often desirable to use instruments which are sufficiently small as to, say, enter a very small aperture such as an aperture in an eye and to manipulate the instrument at various angles relative to the aperture without the necessity of having to enlarge the aperture to any extent. There have elsewhere previously been developed certain instruments which to a certain extent meet this criteria but which are still not completely satisfactory. For example, there have previously been proposed finger operated scissors and forceps which have a handle which can be held in a surgeon's hand. In a previous scissor, the blades are at right angles to the axis of the instrument. Various forceps are known which are finger operated but which have blades which are fixed relative to the axis of the instrument. Such instruments can be satisfactory when the orientation between the operating handle and the operative end is correct but are most unsatisfactory when the necessary angle of operation of the instrument is incorrect relative to the operating handle. For example, a pair of scissors having blades downwardly directed relative to the operative member are perfectly satisfactory when operated downwardly and possibly up to some 45° from downward but are unsatisfactory when it is necessary to operate upwardly or at an angle around the upward direction. Similarly using forceps, if the forceps are operating at an angle from the axis of the instrument, it can be difficult, and possibly dangerous, to attempt to use these at more than 45° from the direction of most comfortable operation.

It is an object of the invention to provide microsurgical instruments which can be finger operated by a surgeon but which, at the same time, can be simply physically located at a required angle to the axis of the handle of the instrument and which are automatically held at the required position whilst the surgical procedure is effected.

In another aspect of the invention I provide a pair of microsurgical scissors which can be finger operated and in which the blades lie in a plane at an angle to the axis of the handle.

The invention broadly includes a finger operated microsurgical instrument having a handle member adapted to be held in a surgeon's hand, a member pivotally connected to the handle member and having a rearwardly directed arm which normally lies at an angle to the handle member and is adapted to be operated by a surgeon, another part of which member extends through a slot in the handle member and contacts a plunger which, on depression of the rearwardly directed arm, moves forwardly and contacts an operable portion of the instrument connected to the handle, which portion is rotatable about the axis of the handle and, wherein, on operation of the rearwardly directed arm, frictional contact retains the instrument in a fixed angular relationship with the handle.

In one aspect of the invention the instrument comprises a pair of microsurgical scissors, one blade of which is formed by or is associated with the outer end of a tubular member and the other blade of which is formed by or is associated with the outer end of a rod within the tubular member, a helical member connected, either directly or indirectly to the inner end of the rod, the helical member passing through a slot formed in a member within the instrument body which body itself is connected to the handle, which member is moveable by a plunger within the handle and on movement causes rotation of the helical member and thus relative rotation of the blades.

The helical member preferably has a compression spring located thereabouts so that when pressure on the bell crank member is released the member within the instrument body is returned to its initial condition thus causing an opposite rotation of the blades.

In another aspect of the invention the instrument comprises forceps which comprise an inner member within a tubular member which is associated with the instrument body and which can be connected to the handle member, the inner member being split and formed at its outer end so that it can move, on operation of the rearwardly directed arm, from a position within the outer member to provide a pair of open jaws which close as they are retracted into the outer member on release of the rearwardly directed arm. These jaws may be formed either with a flat end or with sharp points.

In a still further aspect of the invention I may provide forceps which are at an angle to the axis of the handle, the instrument having an outer tubular member which is formed at its outer end to provide one jaw of the forceps and which has an inner rod which is formed at its outer end to provide the other jaw of the forceps, the arrangement being such that on depression of the rearwardly directed arm the inner member is moved outwardly relative to the tubular member and thus open the forceps and there can be provided means whereby when the arm is released the inner member is driven towards the outer member and the forceps close.

In order that the invention may be more readily understood and put into practice I shall describe several embodiments of microsurgical instruments made in accordance with the invention, the description being in association with the accompanying drawings, in which:

FIG. 1 shows a perspective view of a handle used with the instrument of the invention;

FIG. 2 is a perspective view of scissors adapted to be connected to the handle of FIG. 1;

FIG. 3 is a sectional view of the scissors of FIG. 2 and the forward portion of the handle of FIG. 1;

FIG. 4 is a section similar to that of FIG. 3 but showing the scissors after blade closure;

FIG. 5 is a section along line 5—5 of FIG. 3 looking in the direction of the arrows;

FIG. 6 is a section along line 6—6 of FIG. 3 looking in the direction of the arrows;

FIG. 7 is an end elevation of the scissors of FIG. 3 showing the scissors open;

FIG. 8 is a view similar to FIG. 7 with the scissors closed;

FIG. 9 is a view similar to FIG. 7 showing the orientation of the scissors varied;

FIG. 10 is a section view similar to FIG. 3 but showing a pair of forceps;

FIG. 11 is a view similar to that of FIG. 10 showing the forceps open;

FIG. 12 is an end view of the forceps of FIGS. 10 and 11 showing the alteration of relative orientation of the forceps;

FIG. 13 is the collet or chuck which retains the inner forceps member; and

FIGS. 14 and 15 are two views of an alternative form of forceps.

The instruments to be described are basically designed for ophthalmological use and specifically designed to be able to enter the eye through a very small aperture but have applications in otolaryngological, neurosurgical and other fine microsurgical uses, particularly where the surgery is being done within a body cavity. They are also useful for entomology and botany.

The instruments of the invention are basically designed to enable rotation of the operative portion of the instrument relative to the handle so that the surgeon can, say, hold the instrument in a normal pen or pencil grip and can operate the operable member at the most comfortable position to him whilst the actual angle of operation of the instrument can vary relative to the axis of the handle held by a surgeon, as required. It will be understood that in operations of the type to which the invention is specifically adapted, the surgeon is operating through a microscope and any untoward movement of his hand can cause relatively macro movement of the tip of the instrument and if he is forced to hold his hand in an unnatural position such movements are basically bound to occur.

The invention is specifically related to scissors which cut at a plane at an angle to the axis of the handle, to forceps which also operate in a plane at an angle to the axis of the handle and to forceps which operate along the line of the axis of the handle. In each case the handle used is identical.

The handle 10 basically comprises a member 11 which can be of surgical steel or any other easily sterilisable material, preferably a metal, which handle, at least at its inner end 12, that is the end adjacent which it is gripped, has a hollow bore 13 and preferably has an external thread 14 on its inner end 12. Pivotally attached to the handle there is a bell crank member 15 having a first rearwardly and upwardly directed arm 16, the outer end of which is normally, as illustrated in FIGS. 1 and 3, spaced from the handle by such a distance that it is comfortable for a surgeon to manipulate this arm with his forefinger or any other finger he desires. The other arm 17 of the bell crank passes into the hollow bore 13 of the handle through a slot 18 so that on downward motion of the finger operable arm 16 there is forward motion of the second arm 17. This second arm 17 preferably rests against a plunger member 19 which can move outwardly from the end of the handle 12. Depending upon the arrangement there may be provided, within the handle, a return spring to bring the plunger to its normal condition when the arm of the bell crank operated by the surgeon is released but, preferably, this return is provided on the instrument to be used in association with the handle and it is preferable that the plunger is also associated with the operative portion of the instrument which can pass through the bore 25 of the sleeve 22 and which is provided with an enlarged rear portion which abuts an annular shoulder 27 in the sleeve and is thereby located longitudinally. The rotatable member is retained in the required location longitudinally by means of a ring 28 which can pass over the rotatable member 24, can abut the end of the sleeve 22 and can be there locked by a set-screw. The external surface of this ring may be knurled as it is used to rotate the rotatable member relative to the sleeve 22 and thus the handle 10.

Each form of instrument to be used is provided with an instrument body member which is adapted to be screwed on to the external thread 14 of the handle 10 and which, itself, may be provided with an external thread in order to accept a guard which extends over the instrument when not being used and may be apertured to permit sterilisation of the instrument.

None of the instruments illustrated show an external thread on the body member and in these cases the guard can be a frictional fit over the body.

The first form of instrument I shall describe is a pair of scissors 20 which operate in a plane at an angle to the axis of the handle which scissors can be rotated to any required situation relative to the axis of the handle. These scissors and their operation are illustrated in FIGS. 2 to 9.

The scissors 20 have a body 21 which comprises a fixed sleeve 22 which is internally threaded at 23 at its inner end and which can be connected to the handle and remains in position relative to the handle. Located in this sleeve there is a hollow rotatable member 24. The rotatable member has connected thereto an outwardly directed tube 30 of any required length which tube preferably has an outer diameter of the order of 0.8 mm. The length of the tube depends upon the application in which the scissors are to be used.

The outer end of the tube 30 is formed into one blade 31 of the scissors and thus the tube must be of steel which is sufficiently hardenable to be able to maintain temper.

Located within the tube 30 is a rod 32 which, at its outer end, is provided with the second blade 33 of the scissors, which rod extends rearwardly into a slug 34 located in the rotatable member 24 which uses the counter-bore as a bearing surface. The rod is located by a set screw 35 passing through the slot 36 in the member 24 and it is positioned relative to the outer tube 30 and thus the relative position of the two blades can be adjusted by releasing the set screw, locating the blades and tightening the set screw and also, in this way, the blades may be sharpened when necessary. The slug has affixed to its inner end a helical member 36 circumscribed within the cylindrical bore of the rotatable member and which is formed of a sheet of stainless steel or the like.

Located within the body of the instrument there is a compliment 37 to the plunger 19 which is normally not in contact with the plunger and this compliment has a counter-bored portion 38 adapted to receive the helical member 36' and carries on its outer end a slotted plate 39. The compliment 37 to the plunger is provided with an outwardly directed extension 42 which is located in a slot 43 in the sleeve 22 so the compliment is constrained to move axially.

Between the plate 39 and the slug 34 there is located an helical compression spring 40 which tends to move the assembly to a position adjacent the handle.

The inner end of the helical member 36' may be provided with an extension 41 whereby it is prevented from passing fully through the slot.

In operation of this embodiment when a surgeon depresses the rearwardly directed arm 16 the arm 17 engages the the plunger 19 of the handle which in turn contacts the compliment 37 in the instrument and at that time, depending on the angular location of the scissors for all practical purposes, the angle is locked. The degree of locking is dependant only on the friction between the two plungers, but in practice I find that this is quite sufficient. Thus, provided the angle of the scissors was correct at the time of locking, they will retain this angle.

Further downward pressure on the arm causes the plunger assembly 37 of the instrument to move forward as it is constrained by the extension 42 and thus the slotted plate 39 moves over the helix and causes this to rotate thus causing the slug 34 to rotate and the rod 32 carrying the second scissors blade 33 to rotate so that the scissor action is effected. Depending on the arrangement of the slot 36 in the rotatable member 24, so the degree of rotation is controlled. At the completion of the scissors operation release of the arm 16 will cause the scissors to re-open because of the action of the helical spring 40 between the slotted plate 39 and the plunger assembly 37. Arrangement of the initial position of the blades 31,33 is achieved simply by rotating the ring 28 before the arm 16 is depressed and before frictional contact is made between the plunger 19 and the bell crank arm 17.

In a second embodiment of the invention illustrated in FIGS. 10 to 13 I provide forceps which operate in a plane at an angle to the axis of the handle. In this case the assembly of the body and the rotatable member is similar to that of the last embodiment.

The handle 10 arrangement is identical and again we use a fixed sleeve member 50 which screws on to the threaded end 14 of the handle and through the bore of which passes a hollow rotatable member 51 which is located by a shoulder 52 and a locking ring 53 held in position by a set screw 54.

The hollow rotatable member is associated with with a hollow tube 55 which is formed at its outer end to form one jaw 56 of a pair of forceps which jaw is at an angle to the axis of the tube.

There is provided within the tube 55 a rod 57 which is also formed at its outer end to form the other jaw 58 of the forceps.

The arrangement differs from the previous embodiment in the connection of the rod 57 to the operating mechanism in that there is no requirement for rotational movement of the rod 57 relative to the tube 55.

I provide within the hollow rotatable member 51 a chuck assembly which comprises a chuck 59 located in a logintudinally moveable member 60.

The chuck has a split nose 61 which can receive the rod 57 and which co-operates with a complimentary portion 62 of the longitudinally moveable member 60. This member is normally held in the position illustrated in FIG. 10 by an helical spring 63 and the rod 57 is passed through the tube 55 and into the chuck head 61 and whilst being held a set screw 64 is tightened against the rear of the chuck 59 by a thread 65 in the bore of the longitudinally moveable member. This locks the chuck jaws and holds the rod.

The longitudinally moveable member 60 is provided with an extension 66 which passes along a slot 67 in the rotatable member 51 so the two jaws 56,58 of the forceps are maintained in alignment.

As illustrated the forceps are normally closed but should it be required they could be biased open.

As with the previous embodiment the angular position of the forceps can be adjusted under the microscope and as soon as the plunger of the handle contacts the plunger of the forceps its rotation is effectively prevented and the forceps open. On release of the rear of the extending arm the forceps close and tissue or other matter can be removed or held.

In a still further embodiment illustrated in FIGS. 14 and 15 the invention can be used with forceps which grasp material along the line of the axis of the handle. In this case the outer end 70 of the inner rod 71 is split and formed to provide a pair of arms which may be flat pointed, sharp pointed or formed in any other way and which arms have sufficient springingness to be able to be received within the outer tube 72 and which, when released therefrom can open to provide effective forceps. In this case the outer tube has a plain end but otherwise the instrument is identical to the previous embodiment.

I claim:

1. A finger operated microsurgical instrument comprising a handle and an elongated instrument body rotatably secured within the end of said handle and having a surgical instrument on its other end, plunger means having a substantially flat face reciprocable within the portion of the instrument body which is secured within said handle, an operating bell crank lever pivoted to said handle and having a first arm positioned to be engageable by a surgeon's finger while the handle is held in the surgeon's hand, and a second arm engaging said plunger, an instrument actuating means having a substantially flat face within said instrument body and in frictional face-to-face engagement with said plunger, so that pivotal movement of said first arm by said surgeon will cause reciprocation of saind plunger means against said actuation means and actuation of said instrument, means preventing said actuating means from rotating relative to said instrument body, said instrument body being freely rotatable relative to said handle when said bell crank lever is released, said plunger means and instrument actuating means frictionally securing said instrument body from rotation when said bell crank lever is pivoted in use.

2. A microsurgical instrument as defined in claim 1, wherein a sleeve is rigidly secured to said handle, said instrument body comprising a hollow body portion rotatably engaging said sleeve, said instrument actuating means being slidably received within said hollow body portion and being rotatable therewith, a cavity in said handle, said plunger means being slidable within said cavity to frictionally engage said actuating means on pivotal movement of said bell crank lever.

3. A microsurgical instrument as defined in claim 2, the means preventing said actuating means from rotating relative to said instrument body comprises slot means in said hollow body portion and an extension on said actuating means engaging said slot means.

4. A microsurgical instrument as defined in claim 1, wherein said surgical instrument comprises a pair of microscissors, said instrument body having a tubular extension portion, one blade of said scissors being formed on the end of said extension portion, a rod member within said extension portion, the second blade of said scissors being formed on the free end thereof, a helical member on the other end of said rod member, said instrument actuating means being cooperable with said helical member so that on reciprocation of said actuation means by said plunger means the helical member will rotate causing relative rotation of said blades to effect cutting action.

5. A microsurgical instrument as defined in claim 4, and further including a slug for connecting said helical member to said rod member, said slug having an axial bore receiving said rod member, a set screw passing normally into said slug and said bore for locking the rod member in adjusted position so that said blades are in wiping contact, said slug being in contact with the inside of the instrument body to ensure proper rotation of said rod member with respect to said tubular extension portion.

6. A microsurgical instrument as defined in claim 5, and further including compression spring means in said instrument body engaging between said slug and said actuating means for returning said actuating means, plunger means and bell crank lever to their initial positions when the lever is released by the surgeon, thereby causing an opposite relative rotation of said blades.

7. A microsurgical instrument as defined in claim 1, wherein said surgical instrument comprises forceps, said forceps being oriented at an angle with respect to the longitudinal axis of said handle, said instrument body having an elongated tubular portion formed at its free end as one jaw of the forceps, a rod within said tubular portion and extending from the free end thereof and terminating in a jaw to define the other jaw of said forceps, the other end of said rod being connected to said actuating means for moving the rod outwardly relative to the tubular portion and thus open the forceps, and spring means within said instrument body for biasing the forceps jaws towards a closed position.

8. A microsurgical instrument as defined in claim 7 and further including a chuck held within said actuating means, said other end of said rod being held by said chuck, and screw means within said actuating means for adjusting the location therein of said chuck for adjusting the relationship of said forceps jaws.

9. A microsurgical instrument as defined in claim 1, wherein said surgical instrument comprises forceps, said instrument body having an elongated tubular portion, a rod member within said tubular portion and extending from the free end thereof, said rod member being longitudinally split at its extending end and formed as two jaws, the other end of said rod being connected to said actuating means for moving the rod, and spring return means within said instrument body operable against said actuating means to retract said rod into said tubular portion to close the forceps jaws.

* * * * *